(12) United States Patent
Sugar et al.

(10) Patent No.: US 12,220,369 B2
(45) Date of Patent: Feb. 11, 2025

(54) ASSISTIVE DEVICE FOR PATIENTS WITH SOMATOSENSATION DEFICIENCY

(71) Applicants: Arizona Board of Regents on behalf of Arizona State University, Scottsdale, AZ (US); Dignity Health, San Francisco, CA (US); Luis Lopez, Tolleson, AZ (US)

(72) Inventors: Thomas Sugar, Chandler, AZ (US); Luis Lopez, Tolleson, AZ (US); Lee Griffith, Gilbert, AZ (US); Robin Parmentier, Tempe, AZ (US); Saivimal Sridar, Mesa, AZ (US); Pham Huy Nguyen, Mesa, AZ (US); Jeremy Palmiscno, Phoenix, AZ (US); Will Meredith, Phoenix, AZ (US)

(73) Assignees: Arizona Board of Regents on behalf of Arizona State University, Scottsdale, AZ (US); Dignity Health, San Francisco, CA (US)

( * ) Notice: Subject to any disclaimer, the term of this patent is extended or adjusted under 35 U.S.C. 154(b) by 1146 days.

(21) Appl. No.: 16/858,302

(22) Filed: Apr. 24, 2020

(65) Prior Publication Data

US 2020/0337933 A1 Oct. 29, 2020

Related U.S. Application Data

(60) Provisional application No. 62/838,812, filed on Apr. 25, 2019.

(51) Int. Cl.
*A61H 1/02* (2006.01)
*A61B 5/00* (2006.01)

(52) U.S. Cl.
CPC ......... *A61H 1/0288* (2013.01); *A61B 5/6825* (2013.01); *A61B 2562/0247* (2013.01);
(Continued)

(58) Field of Classification Search
CPC ...... A61H 3/00; A61H 1/0262; A61H 1/0288; A61H 2201/0103; A61H 2201/0153;
(Continued)

(56) References Cited

U.S. PATENT DOCUMENTS 4,807,606 A * 2/1989 Hasegawa ............ A61H 1/0288
128/DIG. 20
7,399,258 B1 7/2008 Sugar et al.
(Continued)

FOREIGN PATENT DOCUMENTS

WO 2004096083 A2 11/2004
WO 2004096905 A2 11/2004
WO 2005074370 A2 8/2005

OTHER PUBLICATIONS

Buscher, G., Koiva, R., Schurmann, C., Haschke, R. and Ritter, H. (2015). Flexible and stretchable fabric-based tactile sensor, Robotics and Autonomous Systems, 63, pp. 244-252.
(Continued)

*Primary Examiner* — Jerrah Edwards
*Assistant Examiner* — Aren Patel
(74) *Attorney, Agent, or Firm* — SNELL & WILMER L.L.P.

(57) ABSTRACT

A soft wearable medical device may comprise a force actuation system at least partially disposed in a glove assembly. The force actuation system may be a passive or active actuation system. The force actuation system may be configured to adjust a grip of a patient during use of the soft wearable medical device. The soft wearable medical device may further comprise a force indication system including a plurality of force sensors and a light array, each force sensor disposed in a finger of the glove assembly and the light array mounted to the glove assembly.

8 Claims, 5 Drawing Sheets

(52) U.S. Cl.
CPC ............... *A61B 2562/0252* (2013.01); *A61B 2562/0261* (2013.01); *A61H 2201/0103* (2013.01); *A61H 2201/0153* (2013.01); *A61H 2201/0157* (2013.01); *A61H 2201/018* (2013.01); *A61H 2201/1638* (2013.01); *A61H 2201/165* (2013.01); *A61H 2201/5056* (2013.01); *A61H 2201/5061* (2013.01); *A61H 2201/5092* (2013.01)

(58) Field of Classification Search
CPC ...... A61H 2201/0157; A61H 2201/018; A61H 2201/1638; A61H 2201/165; A61H 2201/5056; A61H 2201/5061; A61H 2201/5092; A61B 5/6825; A61B 2562/0247; A61B 2562/0252; A61B 2562/0261
See application file for complete search history.

(56) References Cited

U.S. PATENT DOCUMENTS

| | | | |
|---|---|---|---|
| 9,192,487 B2 | 11/2015 | Flaven et al. | |
| 9,308,642 B2 | 4/2016 | Sugar et al. | |
| 9,913,500 B1* | 3/2018 | Matthews | A41D 19/01529 |
| 10,908,708 B1* | 2/2021 | Menendez | G06F 3/0346 |
| 11,009,949 B1* | 5/2021 | Elias | G06F 3/0414 |
| 2009/0131935 A1 | 5/2009 | Yeager | |
| 2011/0302694 A1* | 12/2011 | Wang | A61B 5/6806 2/160 |
| 2013/0085429 A1* | 4/2013 | Nelsen | A61H 9/0078 601/149 |
| 2016/0249695 A1* | 9/2016 | Clemente | A41D 19/002 2/160 |
| 2018/0303698 A1* | 10/2018 | Wijesundara | F15B 15/10 |
| 2020/0121541 A1* | 4/2020 | Wudlick | A61H 1/0288 |
| 2020/0337597 A1 | 10/2020 | Sugar et al. | |
| 2020/0337931 A1 | 10/2020 | Shuch et al. | |
| 2020/0337937 A1 | 10/2020 | Sugar et al. | |

OTHER PUBLICATIONS

About Stroke American Stroke Association.: [Online]. Available: https://www.strokeassociation.org/en/about-stroke.
L. Connell, N. Lincoln, and K. Radford, "Somatosensory impairment after stroke: frequency of different deficits and their recovery," Clinical Rehabilitation, vol. 22, No. 8, pp. 758-767, 2008.
L. M. Carey, T. A. Matyas, and C. Baum, "effects of somatosensory impairment on participation after stroke," Am. J. Occup. Ther., vol. 72, No. 3, p. 6278, 2018.
S. Jones, "Somatosensory Impairment and Balance Dysfunction in Multiple Sclerosis.".
J. M. Blennerhassett, T. A. Matyas, and L. M. Carey, "Impaired Discrimination of Surface Friction Contributes to Pinch Grip Deficit After Stroke," Neurorehabilitation and Neural Repair, vol. 21, No. 3, pp. 263-272, 2007.
"Sensation Testing—Peripheral Nerve Lesion—Rayner & Smale." [Online]. Available: https://www.raynersmale.com/blog/2015/1/17/sensation-testing-for-person-with-peripheral-lesion. [Accessed: Apr. 28, 2019].
Interlink Electronics, "FSR 400 Series Data Sheet" PDS-10004-C datasheet.
"NexGen Ergonomics—Products—Glove Pressure Mapping System." [Online]. Available: http://www.nexgenergo.com/ergonomics/nexglove.html.
SPI, "Matrix Based Tactile Force Sensor, Human Body Interface Pressure Mapping, Body Pressure Map, Pressure Mapping.".
Shull, P. and Damian, D. (2015). Haptic wearables as sensory replacement, sensory augmentation and trainer—a review. Journal of Neuro-Engineering and Rehabilitation, 12(1).
Patterson, P. and Kat, J. (1992). Design and evaluation of a sensory feedback system that provides grasping pressure In a myoelectric hand. The Journal of Rehabilitation research and Development, 29(1), p. 1.
Massy-Westropp, N., Gill, t., Taylor, A., Bohannon, R, and Hill, C. (2011). Hand Grip Strength: age and gender stratified normative data in a population-based study. BMC Research Notes, 4(1).
"Glove Pressure Mapping System." [Online]. Available: http://www.nexgenergo.com/ergonomics/nexglove.html.
"Grip Pressure Sensor Glove." [Online}. Available: https://www.sensorprod.com/dynamic/glove.php.

* cited by examiner

US 12,220,369 B2

ASSISTIVE DEVICE FOR PATIENTS WITH SOMATOSENSATION DEFICIENCY

CROSS-REFERENCE TO RELATED APPLICATIONS

This application is a non-provisional patent application of, and claims priority to, U.S. Provisional Pat. App. No. 62/838,812 filed Apr. 25, 2019 and entitled "Assistive Device for Patients with Somatosensation Deficiency," which is incorporated herein by reference in its entirety (except for any subject matter disclaimers or disavowals, and except to the extent of any conflict with the disclosure of the present application, in which case the disclosure of the present application shall control).

TECHNICAL FIELD

The present disclosure relates to soft robotic systems, and in particular to systems for use by individuals afflicted by neurological conditions.

BACKGROUND

Patients who have suffered through a stroke often have residual neurological deficiencies. Among these deficiencies is sometimes an inability to gauge force in their hand as a result of inadequate motor control. This can have a profound effect on standard of living, as patients have historically inadvertently crushed plastic cups or dropped items because they were not holding on tight enough. As such, a wearable medical device designed to assist daily living remains desirable.

SUMMARY

A soft wearable medical device is disclosed herein. The soft wearable medical device may comprise: a glove assembly; and a force actuation system comprising a first bladder disposed in a palm of the glove assembly, the first bladder configured to displace a fluid in response to displacement of the first bladder. In various embodiments, the fluid displaced in the first bladder can be pushed into a second bladder placed on another portion of the body. Lastly, it is envisioned that the first bladder could be placed on other parts of the body, for example, inside the shoe to measure the pressure against the ground.

The soft wearable medical device may further comprise a force indication system comprising a plurality of force sensors, each force sensor disposed proximate a tip of a finger of the glove assembly. The soft wearable medical device may further comprise attachment strap, wherein: the force indication system further comprises a controller and a light array, the light array mounted to the glove assembly, and the controller housed in the attachment strap. In various embodiments, the controller may be operable to: receive a force measurement from a force sensor in the plurality of force sensors; command a light in the light array to illuminate a first color when the force measurement is below a first force threshold; and command the light in the light array to illuminate a second color when the force measurement is above the first force threshold.

The force actuation system may further comprise an attachment strap, a second bladder and a tube assembly. The first bladder may be in fluid communication with the second bladder via the tube assembly. The second bladder may be configured to contact a patient during use of the soft wearable medical device. The tube assembly may comprise a first tube, a connector, and a second tube. The first tube may be disposed between a first port of the connector and the first bladder. The second tube may be disposed between the second bladder and a second port of the connector. The connector may comprise a third port, and the third port may be sealed. The first bladder may be configured for passive actuation during use of the soft wearable medical device.

A soft wearable medical device is disclosed herein. The soft wearable medical device may comprise: a glove assembly; a force indication system comprising a plurality of force sensors and a light array mounted to the glove assembly, wherein: each force sensor is disposed proximate a tip of a finger of the glove assembly, and each light in the light array is configured to illuminate based on a force measurement of a respective force sensor in the plurality of force sensors.

In various embodiments, the force indication system further comprises a controller in electrical communication with the plurality of force sensors and the light array. The soft wearable medical device may further comprise an attachment strap, wherein the controller is housed in the attachment strap. The controller may be operable to: receive the force measurement from each force sensor in the plurality of force sensors; command a first light in the light array corresponding to a first force sensor in the plurality of force sensors to illuminate a first color when the force measurement of the first force sensor is below a first force threshold; and command the first light in the light array to illuminate a second color when the force measurement of the first force sensor is above the first force threshold. The soft wearable medical device may further comprise a force actuation system configured to adjust a distribution of a palm force during use of the soft wearable medical device. The force actuation system may be a passive force actuation system. The force actuation system may comprise a bladder disposed in a palm of the glove assembly. The glove assembly may comprise an inner glove and an outer glove. The plurality of force sensors may be disposed between the inner glove and the outer glove.

A force indication control system for a soft wearable medical device is disclosed herein. The force indication control system may comprise: a first force sensor in electrical communication with a controller; a second force sensor in electrical communication with the controller; a light array including a first light and a second light, the light array in electrical communication with the controller; and a tangible, non-transitory memory configured to communicate with the controller, the tangible, non-transitory memory having instructions stored thereon that, in response to execution by the controller, cause the controller to perform operations comprising: receiving, by the controller, a first force measurement from the first force sensor; determining, by the controller, whether the first force measurement is below a first force threshold; commanding, by the controller, the first light to illuminate a first color when the first force measurement is below the first force threshold; and commanding, by the controller, the first light to illuminate a second color when the first force measurement is above the first force threshold, wherein the second color is different than the first color.

In various embodiments, the operations may further comprise: receiving, by the controller, a second force measurement from the second force sensor; determining, by the controller, whether the second force measurement is below a second force threshold; commanding, by the controller, the second light to illuminate the first color when the second force measurement is below the second force threshold; and commanding, by the controller, the second light to illuminate the second color when the second force measurement is above the first force threshold, wherein the second color is different than the first color. The force indication control system may further comprise a glove having a thumb and a first finger, wherein the first force sensor is disposed proximate a tip of the thumb, and wherein the second force sensor is disposed proximate a first tip of the first finger. The force indication control system may further comprise a third force sensor in electrical communication with the controller, wherein: the third force sensor disposed proximate a second tip of a second finger of the glove, the first finger is configured to receive an index finger of a patient, and the second finger is configured to receive a middle finger of the patient.

The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting. The contents of this section are intended as a simplified introduction to the disclosure, and are not intended to limit the scope of any claim.

BRIEF DESCRIPTION OF THE DRAWINGS

With reference to the following description and accompanying drawings.

DETAILED DESCRIPTION

The following description is of various exemplary embodiments only, and is not intended to limit the scope, applicability or configuration of the present disclosure in any way. Rather, the following description is intended to provide a convenient illustration for implementing various embodiments including the best mode. As will become apparent, various changes may be made in the function and arrangement of the elements described in these embodiments without departing from principles of the present disclosure.

For the sake of brevity, conventional techniques and components may not be described in detail herein. Furthermore, the connecting lines shown in various figures contained herein are intended to represent exemplary functional relationships and/or physical couplings between various elements. It should be noted that many alternative or additional functional relationships or physical connections may be present in exemplary systems and/or components thereof.

In various exemplary embodiments, patients who have suffered through a stroke often have residual neurological deficiencies. Among these deficiencies is sometimes an inability to gauge force in their hand as a result of inadequate motor control. This can have a profound effect on standard of living, as patients have historically inadvertently crushed plastic cups or dropped items because they were not holding on tight enough. Exemplary embodiments are intended to be, or function as, a wearable medical device designed for assisted daily living. The device eases the burden of individuals dealing with this affliction and thus improves their quality of life.

Exemplary embodiments are intended for use by individuals afflicted by neurological conditions, for example those that cannot sense the force exerted by their hand. The device utilizes a passive system loaded with fluid that translates the force exerted at certain areas of the affected hand, to another location. The device may further provide an increased ability to sense that force and supply that information to the patient. A separate electrical system supplements a light touch threshold of the device and emits a visual cue to expand detection.

Figure 1A:
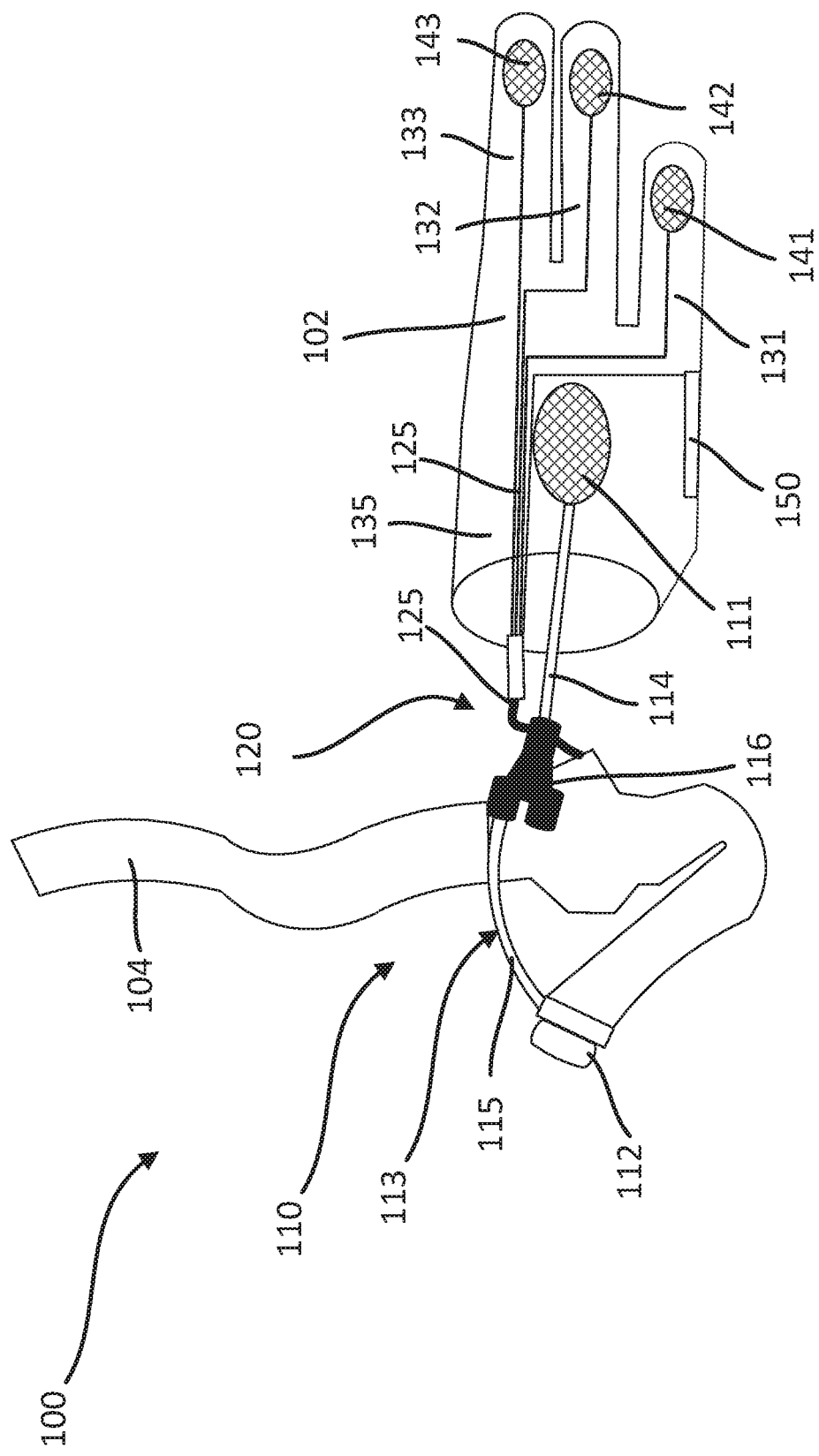
FIG. 1A illustrates a wearable medical device during assembly of the wearable medical device, in accordance with various embodiments.

Referring now to FIG. 1A, a schematic perspective view of a medical device 100 during assembly is illustrated, in accordance with various embodiments. The medical device 100 comprises an inner glove 102, a force actuation system 110, and a force indication system 120. The force actuation system 110 is configured to redistribute a force supplied by a patient of the medical device 100 from one location of a palm to another location of the palm during use of the medical device 100. While disclosed herein as being a passive actuation system, an active actuation for the force actuation system 110 is within the scope of this disclosure. For example, a controller may be coupled to actuators controlling fluid lines to various areas of the inner glove 102 and/or control the actuators in response to a force supplied by the patient based on where additional force would be beneficial. In various embodiments, the force actuation system 110 may provide a more uniform force for a patient via the inner glove 102. In this regard, in accordance with various embodiments, a grip of a patient may become more uniform while the medical device 100 is in use. In various embodiments, a passive actuation system may be cheaper, cost less, and may be lighter than an active actuation system.

In various embodiments, the force indication system 120 may be configured to provide a visual and/or physical indication to a patient to indicate the medical device 100 is functioning properly. For example, in accordance with various embodiments, the force indication system 120 may be configured to provide a visual display of a force supplied in each finger corresponding to a finger of the inner glove 102 by a patient during operation of the medical device 100. Furthermore, in accordance with various embodiments, the force indication system 120 may be configured to provide a physical indication to a patient that the force actuation system is working. For example, the force indication system 120 may be configured to supply a force to a forearm, bicep, tricep, or anywhere on a patient's arm upon attaching the medical device 100 to the patient.

In various embodiments, the inner glove 102 may be comparable to a billiards glove, or the like. For example, in accordance with various embodiments, the inner glove 102 may comprise a thumb 131 and at least one finger (e.g., first finger 132 and/or second finger 133) and an aperture configured to receive a remainder of fingers therethrough. In various embodiments, first finger 132 may correspond to an index finger, and second finger 133 may correspond to a middle finger. Although disclosed herein as being comparable to a billiards glove, any type of glove is within the scope of this disclosure. For example, the glove may comprise anywhere from 1-4 fingers and a thumb 131, in accordance with various embodiments.

In various embodiments, the medical device 100 further comprises an attachment strap 104. The attachment strap 104 may be configured to be coupled to an arm of a patient, for example a forearm of a patient or the like. The attachment strap 104 may comprise any attachment mechanism known in the art, such as a hook and loop fastener, a clip, a hook, or any other fastening attachment mechanism. Although disclosed herein as being coupled to a forearm of a patient, an attachment strap 104 may be configured to couple to any part of a patient's arm, and the medical device 100 is not limited in this regard. The attachment strap 104 may be configured to house, or contain, electrical components of the force indication system 120 and/or the force actuation system 110 of the medical device 100. For example, the attachment strap 104 may house a battery, a microcontroller, a portion of electrical wires, a fluid pump, and/or any other component of a force actuation system 110 or a force indication system 120 of the medical device 100.

In various embodiments, the force actuation system 110 may comprise a first bladder 111 and a tube assembly 113 coupled to the first bladder 111. The first bladder 111 may be configured to receive any fluid therein. In various embodiments, the fluid may be a pneumatic fluid (i.e., an easily compressible gas or liquid), such as compressed air or pure gas. In various embodiments, the fluid may be a low viscosity fluid (e.g., a hydraulic fluid. In various embodiments, the fluid may comprise water. In various embodiments, the first bladder 111 is disposed on a palm 135 of the inner glove 102. In various embodiments, the first bladder 111 may be sized and configured to provide a uniform grip of a patient during use of the medical device 100. In this regard, various sizes and shapes of the first bladder 111 may be utilized to achieve the uniform grip, such as generally spherical, rectangular prismatic, hemi-spherical, cylindrical, concave, convex, or the like.

In various embodiments, the force actuation system 110 may further comprise a second bladder 112. The second bladder 112 may be in fluid communication with the first bladder 111 via the tube assembly 113. Although medical device 100 is illustrated with second bladder 112, the medical device 100 is not limited in this regard. For example, a reservoir or a pump may replace the second bladder and be stored in the attachment strap 104, in accordance with various embodiments. The second bladder 112 may be coupled to the attachment strap 104. In this regard, in accordance with various embodiments, the second bladder 112 may act as a part of the force indication system 120. For example, the second bladder 112 may be configured to inflate when the first bladder 111 is compressed, such as when a patient wears inner glove 102 and/or when a patient is grabbing an object with the inner glove 102. As such, the second bladder 112 may be configured to apply pressure to a forearm of a patient in response to the compressing the first bladder 111. In various embodiments, bladders 111, 112 are made of specialized plastic and protected by a specially designed plastic wrap. Bladders 111, 112 will be sealed except for a single point where a barbed fitting is inserted and secured. The fitting protrudes through the plastic and the canvas such that the tube assembly 113 can be attached to the system.

In various embodiments, the tube assembly 113 may comprise a first tube 114, a second tube 115, and a connector 116. The first tube 114 may extend from the first bladder 111 to the connector 116. Similarly, the second tube 115 may extend from the connector 116 to the second bladder 112.

The connector 116 may comprise a three-way junction. In this regard, during manufacturing of the medical device, the fluid may be laded into the first bladder 111 via an inlet of the junction, and the inlet of the junction may be sealed thereafter. Although illustrated as comprising two tubes and a connector, various fluid assemblies may be readily apparent to one skilled in the art, and the present disclosure is not limited in this regard. For example, the fluid may be loaded into the first bladder and a single tube may be coupled to the first bladder 111 and the second bladder 112, in accordance with various embodiments. In accordance with various embodiments, the tube 115 maybe connected to a second and/or a third bladder to create a pressure on multiple places of the body.

In a passive system, when the first bladder 111 is squeezed, fluid or air moves from tubes 114 and 115 to transfer the pressure and increase the size of the second bladder 112. This second bladder 112 can push on another part of the body where the user still has sensation and proprioception. In this way the measured pressure in the first bladder 111 is transferred to a second position that can be felt by the patient. This is a general method of substituting the lost sensation in one body part to be felt and measured at a secondary position on the body. In various embodiments, this can be used at the hand or at the foot.

In various embodiments, the force indication system 120 comprises a first force sensor 141. The first force sensor 141 may be disposed on the thumb 131 of inner glove 102 proximate a tip of the thumb 131. The first force sensor 141 is configured to measure a force supplied by a patient during use of the medical device 100. The first force sensor 141 may be in electrical communication with a microcontroller via wires 125, as described further herein. At least one wire in the wires 125 may extend from the first force sensor 141 to the microcontroller, which may be housed in the attachment strap 104. The wires 125 may be contained in a wiring harness or any other harness configured to contain and/or insulate wires. In various embodiments, the first force sensor 141 may comprise a force sensitive resistor, a force sensitive capacitor, a piezoelectric force sensor, or any other force sensor known in the art. Preferably, the first force sensor 141 comprises a force sensitive resistor. The microcontroller receives data from first force sensor 141 and interprets the data into a signal for a light array 150 to utilize, as described further herein. Although the first force sensor 141 is illustrated as communicating with a microcontroller via wires 125, wireless communications are also within the scope of this disclosure.

In accordance with various embodiments, the force indication system 120 may further comprise a second force sensor 142 and a third force sensor 143. The second force sensor 142 and the third force sensor 143 may be in accordance with the first force sensor 141. The second force sensor 142 may be disposed in the first finger 132 (e.g., the index finger), and the third force sensor 143 may be disposed in the second finger 133 (e.g., the middle finger). In various embodiments, the number of force sensors may correspond to the number of fingers of inner glove 102. In various embodiments, a glove may have more fingers than force sensors. For example, the first force sensor 141 and the second force sensor 142 disposed in a five-finger glove is within the scope of this disclosure. Various force sensor and finger combinations may be readily apparent to one skilled in the art, and the present disclosure is not limited in this regard.

In accordance with various embodiments, the force indication system 120 further comprises the light array 150. The light array 150 may be in electrical communication with the microcontroller disposed in the attachment strap 104. In various embodiments, the light array 150 may be disposed proximate a thumb side (e.g., proximate thumb 131) of the palm 135 of inner glove 102. The light array 150 may be configured to provide a patient with an indication of a force being applied by a respective finger of inner glove 102. For example, the light array 150 may comprise a light corresponding to each force sensor (e.g., first force sensor 141, second force sensor 142, and third force sensor 143).

Figure 1B:
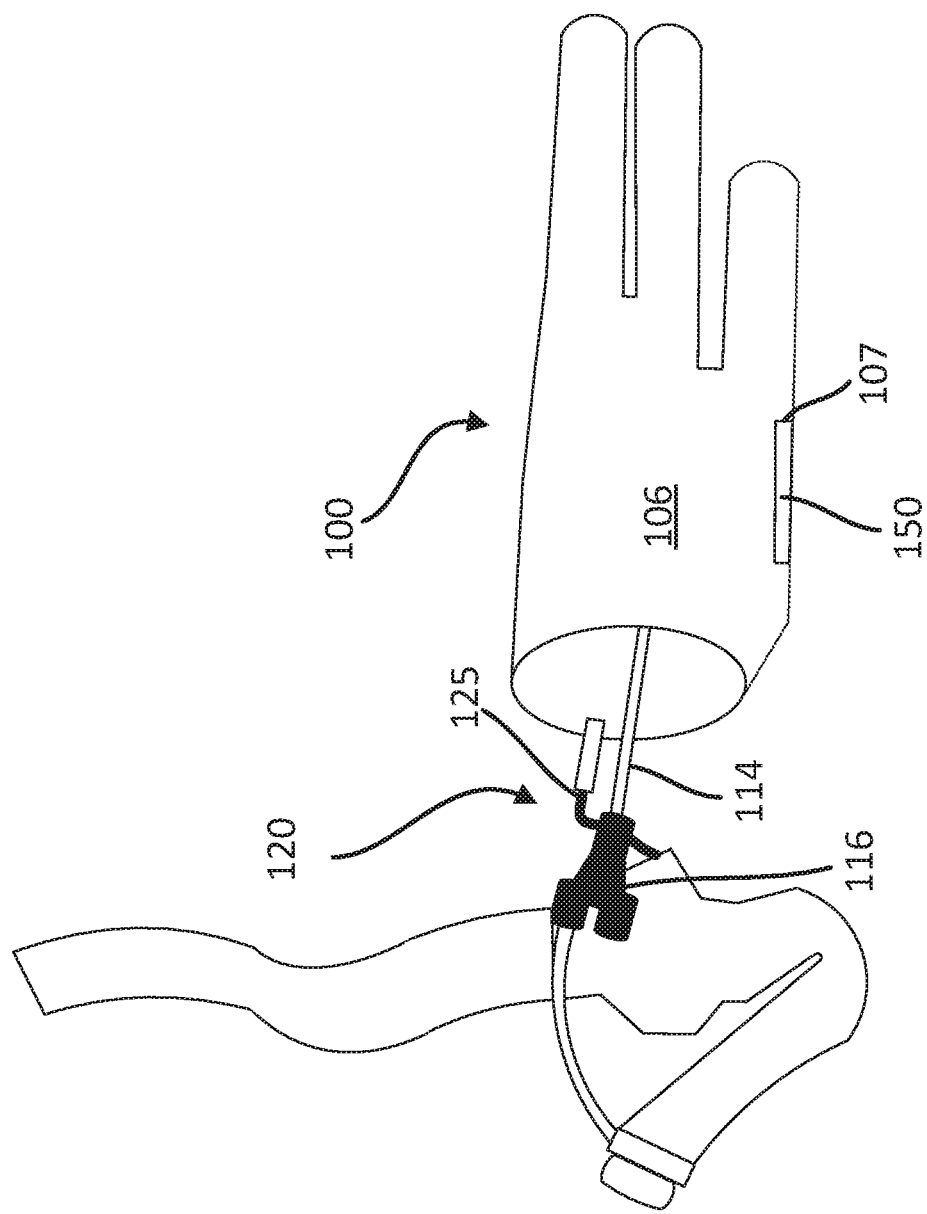
FIG. 1B illustrates an assembled wearable medical device, in accordance with various embodiments.

Referring now to FIG. 1B, a schematic perspective view of the medical device 100 fully assembled is illustrated, in accordance with various embodiments. The medical device 100 may further comprise an outer glove 106. The outer glove 106 may be disposed over the inner glove 102 from FIG. 1 and form a glove assembly 101. With combined reference to FIGS. 1A and 1B, the glove assembly 101 may comprise the inner glove 102, the outer glove 106, the first force sensor 141, the second force sensor 142, the third force sensor 143, the first bladder 111, the light array 150, and/or a portion of wires 125. In various embodiments, the first force sensor 141, the second force sensor 142, the third force sensor 143, and the first bladder 111 may be disposed between inner glove 102 and outer glove 106. In this regard, the glove assembly 101 may house the sensors and the first bladder 111. In various embodiments, the outer glove 106 may comprise an aperture 107 configured to receive the light array 150. In various embodiments, the light array 150 may be mounted to the outer glove 106. The light array 150 may be coupled to the outer glove 106 in any manner, as long as the light array 150 may be visible to a patient during use of the medical device 100. In this regard, the light array 150 may be configured to be visible to a patient during use of the medical device 100.

Figure 2:
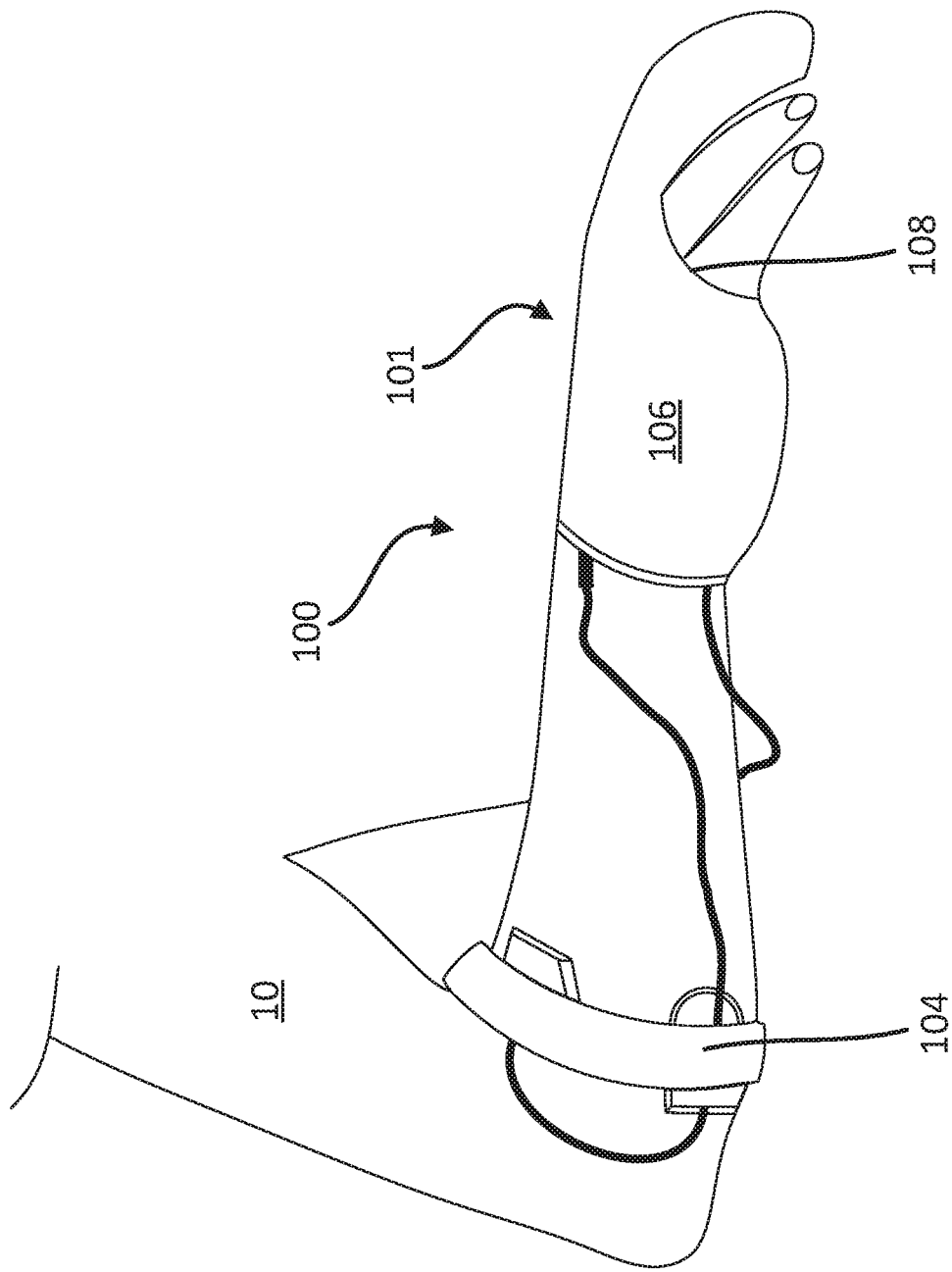
FIG. 2 illustrates a perspective view of a wearable medical device in use, in accordance with various embodiments.

Referring now to FIG. 2, the medical device 100 in use by a patient 10 is illustrated, in accordance with various embodiments. With combined reference to FIGS. 1A and 2, a finger aperture 108 may be disposed through inner glove 102 and outer glove 106. The finger aperture 108 may be configured to receive a pinky finger and/or a ring finger of the patient 10. In various embodiments, while a patient 10 is grabbing various items, only a few fingers and a thumb may be utilized, and the pinky finger/ring finger may provide little support to grabbing a respective item. As such, in accordance with various embodiments, the finger aperture 108 may be provided to increase air circulation within the glove assembly 101, to prevent the glove assembly 101 from being too hot, and/or to prevent the patient from sweating. In various embodiments, the attachment strap 104 may be coupled proximate a forearm of the patient 10.

Figure 3:
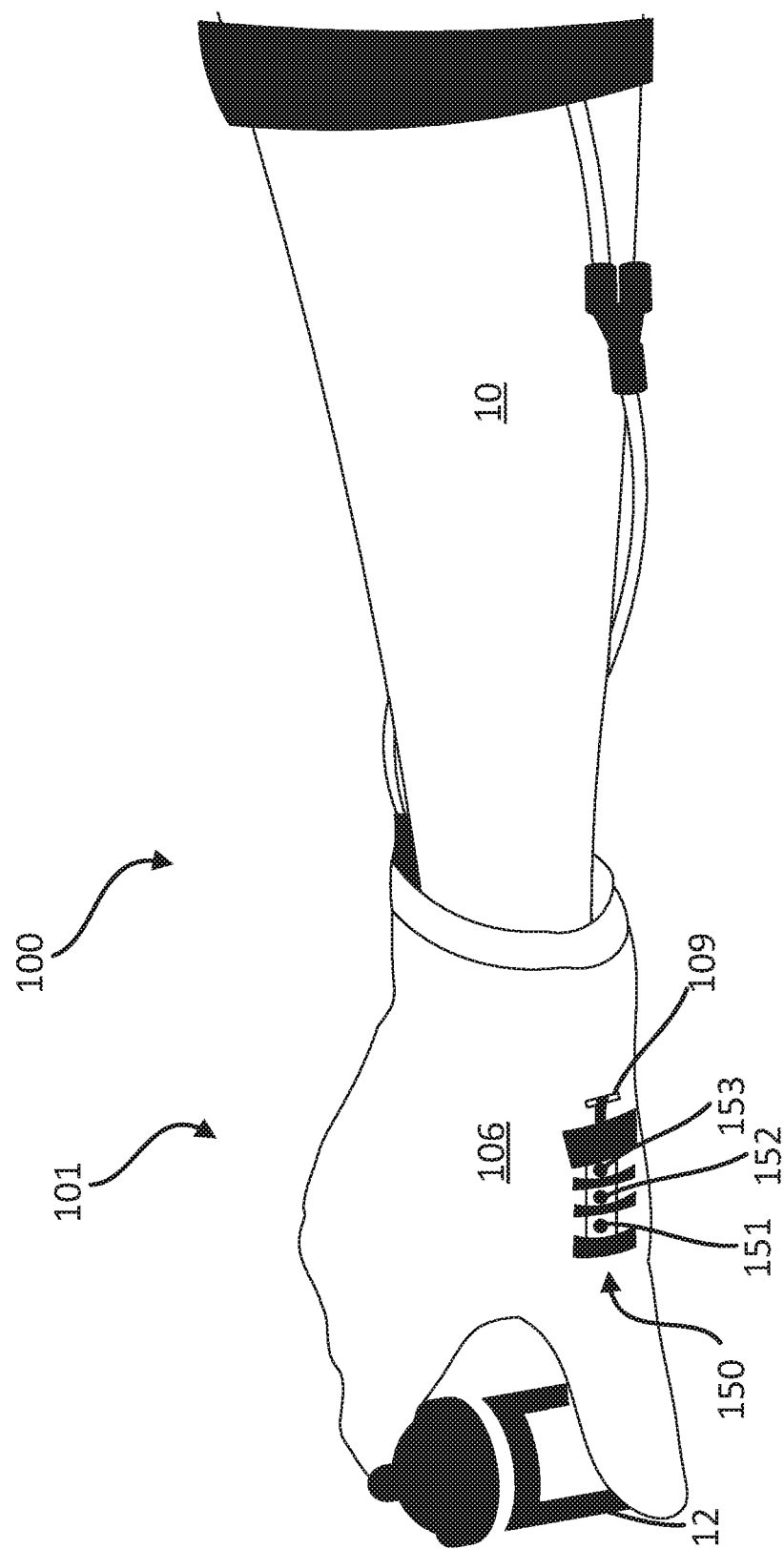
FIG. 3 illustrates a perspective view of a wearable medical device in use, in accordance with various embodiments.

Referring now to FIG. 3, the medical device 100 in use by a patient 10 is illustrated in accordance with various embodiments. In various embodiments, the light array 150 is mounted externally on outer glove 106. A wire from wires 125 may be coupled to the light array 150 and extend through a wire aperture 109 of outer glove 106 into glove assembly 101. The light array 150 may be mounted proximate a thumb portion of outer glove 106. In this regard, the light array 150 may face the patient 10 while the patient is grabbing an item (e.g., item 12).

In various embodiments, the light array 150 comprises a first light 151, a second light 152, and a third light 153. The first light 151 may be electrically coupled to the microcontroller and configured to illuminate based on a force measured by first force sensor 141 from FIG. 1A. Similarly, second light 152 may be electrically coupled to the microcontroller and configured to illuminate based on a force measured by second force sensor 142, and the third light 153 may be electrically coupled to the microcontroller and configured to illuminate based on a force measured by third force sensor 143 from FIG. 1A. A light array 150 as described herein may comprise any light display, such as incandescent, fluorescent, halogen, or the like. In various embodiments, the light array 150 may preferably comprise a light emitting diode (LED) array. In various embodiments, the light array 150 may provide the patient 10 with visual cues as to the level of force the patient is applying to the item 12. In this regard, a patient may adjust the level of force based on the color displayed by the light array for a respective finger in the glove assembly 101.

Figure 4:
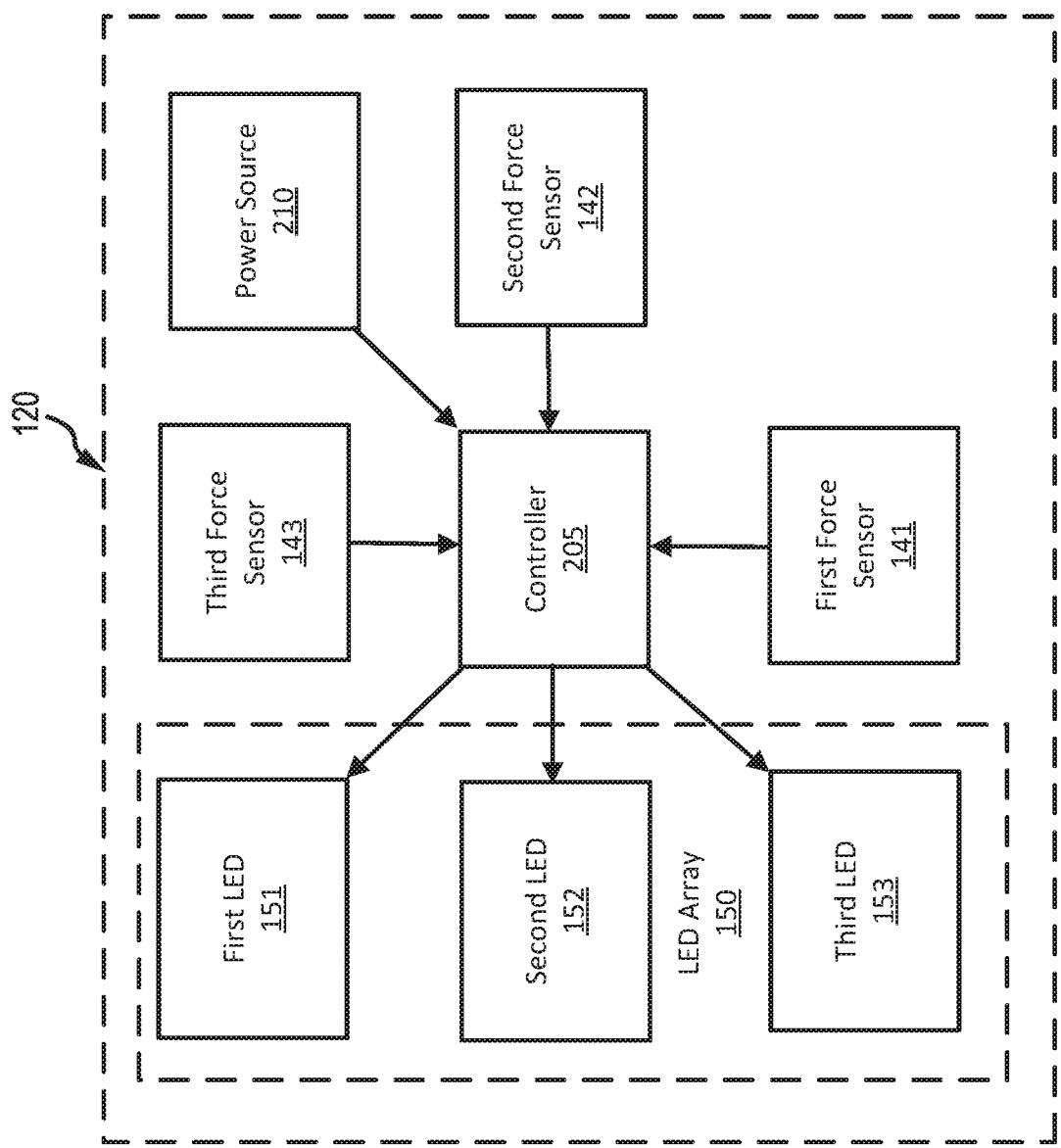
FIG. 4 illustrates a force indication system for use in a wearable medical device, in accordance with various embodiments.

Referring now to FIG. 4, a schematic block diagram of a force indication system 120 for use in the medical device 100 from FIGS. 1A-3 is illustrated, in accordance with various embodiments. Force indication system 120 includes a controller 205 in electrical communication with the first force sensor 141, the second force sensor 142, the third force sensor 143, a power source 210, and a light array 150. In various embodiments, controller 205 may be integrated into a microcontroller disposed within the attachment strap 104 from FIG. 1A. In various embodiments, controller 205 may be configured as a central network element or hub to access various systems and components of force indication system 120. Controller 205 may comprise a network, computer-based system, and/or software components configured to provide an access point to various systems and components of force indication system 120. In various embodiments, controller 205 may comprise a processor. In various embodiments, controller 205 may be implemented in a single processor. In various embodiments, controller 205 may be implemented as and may include one or more processors and/or one or more tangible, non-transitory memories and be capable of implementing logic. Each processor can be a general purpose processor, a digital signal processor (DSP), an application specific integrated circuit (ASIC), a field programmable gate array (FPGA) or other programmable logic device, discrete gate or transistor logic, discrete hardware components, or any combination thereof. Controller 205 may comprise a processor configured to implement various logical operations in response to execution of instructions, for example, instructions stored on a non-transitory, tangible, computer-readable medium configured to communicate with controller 205. In various embodiments, the power source 210 may comprise a battery.

System program instructions and/or controller instructions may be loaded onto a non-transitory, tangible computer-readable medium having instructions stored thereon that, in response to execution by a controller, cause the controller to perform various operations. The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in *In Re Nuijten* to fall outside the scope of patentable subject matter under 35 U.S.C. § 101.

In various embodiments, the light array 150 comprises a first light 151, a second light 152, and a third light 153. Each light in the light array 150 may correspond to a respective force sensor. For example, first force sensor 141 may correspond to first light 151, second force sensor 142 may correspond to second light 152, and third light 153 may correspond to third force sensor 143. In various embodiments, the light array 150 comprises a number of LEDs corresponding to the number of force sensors of the respective medical device 100 from FIGS. 1A-3. For example, when two force sensors are used, two LEDs in a light array may be used. In this regard, a patient may be provided a visual indication of a force supplied by a respective finger corresponding to reading from each force sensor of the medical device 100 from FIGS. 1A-3.

In various embodiments, the first force sensor 141 is configured to measure a force supplied by a patient proximate a tip of thumb 131 of the inner glove 102 from FIG. 1A. In response to measuring the force, the controller 205 may interpret the measured force and supply a signal to the first light 151 in the light array 150. The signal supplied to the light array 150 may illuminate proportionate to a force supplied by the thumb of a patient at proximate the tip of thumb 131 of the inner glove 102. For example, if the measured force is below a first force threshold, the first light 151 may illuminate a first color (e.g., red). If the measured force is above the first force threshold and below a second force threshold, the first light 151 may illuminate a second color (e.g., yellow). If the measured force is above the second force threshold, the first light 151 may illuminate a third color (e.g., green). Any number of colors arranged in any order may be a design choice and one skilled in the art may recognize several color orders and be within the scope of this disclosure. For example, an additional force threshold may be provided between the first force threshold and the second force threshold and correspond to a fourth color (e.g., orange).

In various embodiments, the second force sensor 142 is configured to measure a force supplied by a patient proximate a tip of first finger 132 (e.g., index finger) of the inner glove 102 from FIG. 1A. In response to measuring the force, the controller 205 may interpret the measured force and supply a signal to the second light 152 in the light array 150. The second light 152 may be in accordance with the first light 151 as described herein.

In various embodiments, the third force sensor 143 is configured to measure a force supplied by a patient proximate a tip of second finger 133 (e.g., middle finger) of the inner glove 102 from FIG. 1A. In response to measuring the force, the controller 205 may interpret the measured force and supply a signal to the third light 153 in the light array 150. The third light 153 may be in accordance with the first light 151 and/or second light 152 as described herein.

An exemplary embodiment is a system intended for use in gauging the force exerted by the hand. Certain stroke patients or individuals suffering from similar neurological trauma sometimes lose an ability to gauge the grip strength of their hand and have trouble adjusting to life. Patients have used as an example the fact that they often crush disposable cups due to this affliction. Through the use of sensors and actuators, this product has been able to solve that specific problem. It has a potential to increase their quality of life and, by extension, the secondary and tertiary symptoms associated with the affliction, such as depression.

While the principles of this disclosure have been shown in various embodiments, many modifications of structure, arrangements, proportions, the elements, materials and components, used in practice, which are particularly adapted for a specific environment and operating requirements may be used without departing from the principles and scope of this disclosure. These and other changes or modifications are intended to be included within the scope of the present disclosure.

The present disclosure has been described with reference to various embodiments. However, one of ordinary skill in the art appreciates that various modifications and changes can be made without departing from the scope of the present disclosure. Accordingly, the specification is to be regarded in an illustrative rather than a restrictive sense, and all such modifications are intended to be included within the scope of the present disclosure. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element.

As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. Also, as used herein, the terms "coupled," "coupling," or any other variation thereof, are intended to cover a physical connection, an electrical connection, a magnetic connection, an optical connection, a communicative connection, a functional connection, and/or any other connection. When language similar to "at least one of A, B, or C" or "at least one of A, B, and C" is used in the specification or claims, the phrase is intended to mean any of the following: (1) at least one of A; (2) at least one of B; (3) at least one of C; (4) at least one of A and at least one of B; (5) at least one of B and at least one of C; (6) at least one of A and at least one of C; or (7) at least one of A, at least one of B, and at least one of C.

What is claimed is:

1. A soft wearable medical device for treatment of a somatosensation deficiency in a hand, comprising:
    a glove assembly;
    a force actuation system comprising a first bladder and a second bladder, the first bladder disposed in a palm of the glove assembly, wherein:
        the first bladder is configured to displace a fluid in response to displacement of the first bladder, and
        the second bladder in fluid communication with the first bladder via a tube assembly, the second bladder disposed proximate a forearm of a user when the glove assembly is placed on the hand of the user having the somatosensation deficiency in the hand;
    a force indication system comprising a controller, a light array, and a plurality of force sensors, wherein each of the plurality of force sensors is disposed proximate a tip of a finger of the glove assembly, and wherein the light array is mounted to the glove assembly; and
    an attachment strap, wherein the controller is housed in the attachment strap, and wherein the controller is operable to:
        receive a force measurement from one of the plurality of force sensors;
        command a light in the light array to illuminate a first color when the force measurement is below a first force threshold; and
        command the light in the light array to illuminate a second color when the force measurement is above the first force threshold.

2. The soft wearable medical device of claim 1, wherein each light in the light array is configured to illuminate based on the force measurement of a respective force sensor in the plurality of force sensors.

3. The soft wearable medical device of claim 1, wherein the first bladder is configured for passive actuation during use of the soft wearable medical device.

4. The soft wearable medical device of claim 1, wherein the force actuation system is configured to adjust a distribution of a palm force during use of the soft wearable medical device.

5. The soft wearable medical device of claim 4, wherein the force actuation system is a passive force actuation system.

6. The soft wearable medical device of claim 4, wherein the glove assembly comprises an inner glove and an outer glove, and wherein the plurality of force sensors are disposed between the inner glove and the outer glove.

7. The soft wearable medical device of claim 1, wherein, responsive to compression of the first bladder, a portion of the fluid is displaced into the second bladder via the tube assembly to apply a force to the forearm of the user.

8. A method for assisting a user having the somatosensation deficiency in the hand, the method comprising:
- coupling the soft wearable medical device of claim 7 to the hand of the user having the somatosensation deficiency;
- compressing, by the user, the first bladder by grasping an object with the hand, wherein the compressing displaces the portion of the fluid into the second bladder; and
- inflating, by the displacement of the portion of the fluid, the second bladder to apply the force to the forearm of the user, the force proportional to the compression of the first bladder.

* * * * *